(12) United States Patent
Petereit et al.

(10) Patent No.: US 7,160,558 B2
(45) Date of Patent: *Jan. 9, 2007

(54) COATING AND BINDING AGENT FOR PHARMACEUTICAL FORMULATIONS WITH IMPROVED STORAGE STABILITY

(75) Inventors: Hans-Ulrich Petereit, Darmstadt (DE); Christian Meier, Darmstadt (DE); Erna Roth, Darmstadt (DE)

(73) Assignee: Roehm GmbH & Co. KG, Darmstadt (DE)

( * ) Notice: Subject to any disclaimer, the term of this patent is extended or adjusted under 35 U.S.C. 154(b) by 419 days.

This patent is subject to a terminal disclaimer.

(21) Appl. No.: 10/239,634

(22) PCT Filed: Feb. 27, 2001

(86) PCT No.: PCT/EP01/02018

§ 371 (c)(1),
(2), (4) Date: Sep. 24, 2002

(87) PCT Pub. No.: WO02/067906

PCT Pub. Date: Sep. 6, 2002

(65) Prior Publication Data

US 2003/0064036 A1    Apr. 3, 2003

(51) Int. Cl.
*A61K 9/14*    (2006.01)
*A61K 9/16*    (2006.01)

(52) U.S. Cl. ........................ 424/489; 424/490
(58) Field of Classification Search ................ 424/489, 424/490, 491–495
See application file for complete search history.

(56) References Cited

U.S. PATENT DOCUMENTS

| | | | | |
|---|---|---|---|---|
| 3,957,966 A | * | 5/1976 | Valan ........................ | 424/482 |
| 4,341,563 A | * | 7/1982 | Kurihara et al. ......... | 106/174.1 |
| 4,483,846 A | * | 11/1984 | Koide et al. ................. | 424/433 |
| 4,835,142 A | * | 5/1989 | Suzuki et al. ................. | 514/53 |
| 5,342,646 A | | 8/1994 | Kleese et al. | |
| 5,578,316 A | * | 11/1996 | Bhardwaj et al. ........... | 424/441 |
| 5,730,999 A | | 3/1998 | Lehmann et al. | |
| 5,993,849 A | | 11/1999 | Assmus et al. | |
| 6,248,363 B1 | * | 6/2001 | Patel et al. .................. | 424/497 |
| 6,306,428 B1 | | 10/2001 | Lehmann et al. | |
| 6,576,255 B1 | | 6/2003 | Petereit et al. | |
| 6,624,210 B1 | * | 9/2003 | Petereit et al. .............. | 523/102 |
| 6,846,891 B1 | | 1/2005 | Petereit et al. | |
| 2002/0007769 A1 | * | 1/2002 | Yoshioka et al. ........... | 106/403 |

FOREIGN PATENT DOCUMENTS

| | | |
|---|---|---|
| EP | 1 125 586 A1 | 8/2001 |
| WO | WO 99/09104 | 2/1999 |
| WO | WO 00/05307 | 2/2000 |
| WO | WO 00/24423 | 5/2000 |

* cited by examiner

*Primary Examiner*—S. Tran

(57) ABSTRACT

The invention relates to a process for the preparation of a coating and binding agent for oral or dermal pharmaceutical forms, essentially consisting of (a) a copolymer consisting of free-radical-polymerized C1 to C4 esters of acrylic or methacrylic acid and further (meth)acrylate monomers which contain functional tertiary ammonium groups, the coplymer being present in powdered form having an average particle size of 1–40 μm, (b) 3 to 15% by weight, based on (a), of an emulsifier having an HLB of at least 14 and (c) 5 to 50% by weight, based on (a), of a $C_{12}$—to $C_{18}$-monocarboxylic acid or a $C_{12}$—to $C_{18}$-hydroxyl compound, the components (a), (b) and (c) being blended or mixed with one another with or without addition of water and if appropriate with addition of a pharmaceutical active compound and further customary additives and the coating and binding agent being produced from the mixture by melting, casting, spreading or spraying. The invention further relates to the coating and binding agent itself.

20 Claims, No Drawings

COATING AND BINDING AGENT FOR PHARMACEUTICAL FORMULATIONS WITH IMPROVED STORAGE STABILITY

The invention relates to a coating and binding agent for pharmaceutical formulations having improved storage stability.

PRIOR ART

WO 00/05307 describes a process for the production of a coating and binding agent for oral or dermal pharmaceuticals consisting of (a) 35–98% by weight of a copolymer consisting of free-radical-polymerized C1- to C4-esters of acrylic or methacrylic acid and further (meth)acrylate monomers which have functional tertiary ammonium groups and (b) 1–50% by weight of a plasticizer and 1–15% by weight of an emulsifier having an HLB of at least 14, the components (a), (b) and (c) being blended with one another with or without addition of water and optionally with addition of a pharmaceutical active compound and further customary additives and the coating and binding agent being produced by melting, casting, spreading or spraying, the copolymer (a) being incorporated in powder form having an average particle size of 1–40 μm.

The formulation in the defined powder form in combination with plasticizer and emulsifier makes it possible to convert the corresponding copolymers into stable aqueous solutions or dispersions without the addition of acids. There is the advantage that an otherwise occuring bitter intrinsic taste of the coating agent can be avoided. The coating and binding agents are moreover hardly soluble in water, but dissolve rapidly in artificial gastric juice. They are therefore particularly suitable for taste-isolating formulations which rapidly decompose in the gastric juice. No details are contained on the water permeability of the coatings.

OBJECT AND ACHIEVEMENT

While a whole series of pharmaceutical active compounds are very stable in dry air, they are sensitive to moisture and moisture-related pH shifts in the alkaline pH range. The storage conditions for coated or bound pharmaceutical formulations are not optimum everywhere, so that, for example, in tropical regions it can perfectly well occur that such pharmaceutical formulations are exposed to relatively high atmospheric humidities over a relatively long period before use. It is therefore generally important that as little moisture as possible can penetrate through the pharmaceutical coatings or binding agents to the enclosed active compound. It was therefore seen as an object to make available coating and binding agents for oral or dermal pharmaceutical forms which guarantee a good isolation against the penetration of atmospheric humidity.

The invention starts essentially from WO 00/05307. The coating and binding agents described there are in particular to be further developed to the effect that their water vapour permeability is improved without the other properties such as rapid disintegration in artificial gastric juice and good processability being adversely affected.

The object is achieved by a process for the production of a coating and binding agent for oral or dermal pharmaceutical forms consisting essentially of (a) a copolymer consisting of free-radical-polymerized C1- to C4-esters of acrylic or methacrylic acid and further (meth)acrylate monomers which have functional tertiary amino groups, the copolymer being present in the powder form having an average particle size of 1–40 μm (b) 3 to 15% by weight, based on (a), of an emulsifier having an HLB of at least 14

(c) 5 to 50% by weight, based on (a), of a $C_{12}$- to $C_{18}$-monocarboxylic acid or a $C_{12}$- to $C_{18}$-hydroxyl compound the components (a), (b) and (c) being blended or mixed with one another with or without addition of water and optionally with addition of a pharmaceutical active compound and further customary additives and the coating and binding agent being produced from the mixture by melting, casting, spreading, spraying or granulating.

While coating and binding agents according to WO 00/05307 have water vapour permeabilities measured according to DIN 53 122 in the range of 400 $(g/m^2/d)$ or above, the coating and binding agents according to the invention lie at water vapour permeabilities of at most 350 $(g/m^2/d)$, preferably at most 300 $(g/m^2/d)$, particularly preferably at most 200 $(g/m^2/d)$. It was not foreseeable that it would be possible to achieve this effect by the combination of the components (a), (b) to [sic] (c) without the known advantageous properties of coating and binding agents according to WO 00/05307 being adversely affected. In particular, the use of the component (c) also makes possible extensive or complete relinquishment of customary plasticizers. This is a further advantage, as efforts are always made to keep the number of the components in pharmaceutical formulations low.

CARRYING OUT THE INVENTION

Component (a)

The copolymers (a) consist essentially or entirely of free-radical-polymerized C1 to C4 esters of acrylic or methacrylic acid and further (meth)acrylate monomers which contain functional tertiary amino groups.

Suitable monomers having functional tertiary amino groups are listed in U.S. Pat. No. 4,705,69, column 3, line 64 to column 4, line 13. Particular mention may be made of dimethylaminoethyl acrylate, 2-dimethylaminopropyl acrylate, dimethylaminopropyl methacrylate, dimethyl-aminobenzyl acrylate, dimethylaminobenzyl methacrylate, (3-dimethylamino-2,2-dimethly)propyl acrylate, dimethylamino-2,2-dimethly)propyl methacrylate, (3-dimethylamino-2,2-dimethly)propyl acrylate and diethylamino-2,2-dimethly)propyl methacrylate. Dimethylaminoethyl methacrylate is particularly preferred.

The content of the monomers having tertiary amino groups in the copolymer can advantageously be between 30 and 70% by weight, preferably between 40 and 60% by weight. The proportions of the C1 to C4 esters of acrylic or methacrylic acid is 70–30% by weight. Mention may be made of methyl methacrylate, ethyl methacrylate, butyl methacrylate, methyl acrylate, ethyl acrylate, butyl acrylate.

A (meth)acrylate copolymer having tertiary amino groups corresponding to component (a) can be synthesized, for example, from 20–30% by weight of methyl methacrylate, 20–30% by weight of butyl methacrylate and 60–40% by weight of dimethylaminoethyl methacrylate. The proportion of component (a) in the formulation is preferably 50–90% by weight.

The copolymers (a) are obtained in a manner known per se by free-radical substance, solution, bead or emulsion polymerization. They must be brought into the particle size range according to the invention before processing by means of suitable grinding, drying or spraying processes. Suitable equipment for the production of the powders is familiar to the person skilled in the art, e.g. air-jet mills, pinned disc mills, fan mills. If desired, appropriate screening steps can be included. A suitable mill for large industrial amounts is, for example, a counter-jet mill (Multi No. 4200) which is operated at about 6 bar overpressure.

The average particle size of the powders can be determined as follows:

By means of air-jet screening for the simple division of the ground product into a few fractions. This method is somewhat more inaccurate in this measuring range than the alternatives. At least 70, preferably 90, % of the particles based on the mass (mass distribution), however, should be in the size range according to the invention of 1–40 μm, preferably 10–30 μm.

A highly suitable measuring method is laser scattering for determination of the particle size distribution. Commercial apparatuses allow measurement in air (Malvern S3.01 particle sizer) or preferably in liquid media (LOT, Galai CIS 1). The prerequisite for measurement in liquids is the the polymer does not dissolve therein or the particles change in another manner during the measurement. A suitable medium is, for example, a highly diluted (about 0.02% strength) aqueous polysorbate 80 solution. The average particle diameter must be in the range between 1 to 40, preferably between 5 and 35, in particular between 10 and 20 μm.

Component (b)

Emulsifiers or surfactants are surface-active substances having lyobipolar character, i.e. non-polar, lipophilic and polar, hydrophilic centres must be present in their molecule (P. H. List, Arzneiformen-lehre, Wissenschaftliche Verlagsgesellschaft mbH Stuttgart, 1982, Chap. 6.2.). Depending on the molecular structure, a differentiation is made between ionic and non-ionic emulsifiers.

The HLB is a measure of the hydrophilicity or lipophilicity of non-ionic surfactants introduced in 1950 by Griffin. It can be determined experimentally by means of the phenol titration method according to Marszall; cf. "Parfümerie, Kosmetik" (Perfumery, Cosmetics), Volume 60, 1979, pp. 444–448; further references in Römpp, Chemie-Lexikon, 8$^{th}$ Edition 1983, p. 1750. Furthermore see, for example, U.S. Pat. No. 4,795,643 (Seth)).

An HLB (Hydrophilic/Lipophilic Balance) can only be determined exactly in the case of non-ionic emulsifiers. In the case of anionic emulsifiers, this value can be determined arithmetically, but is virtually always above or far above 14.

Emulsifiers (b) having an HLB of below 14 are understood according to the invention as meaning hydrophilic, non-ionic emulsifiers having an HLB range of at least 14, and likewise hydrophilic, anionic emulsifiers and their salts which have an arithmetic HLB of over 14. Emulsifiers having HLBs of less than 14, such as, for example, glycerol monostearate, can indeed additionally also be contained, but do not replace the emulsifiers (b) having HLBs of at least 14. Suitable emulsifiers (b) are, for example, sodium laurylsulphate and sodium cetylstearylsulphate, sucrose stearate and polysorbate 80. The emulsifiers (b) are present in amounts of 1–15, preferably 5–10, % by weight, based on component (a). Also possible, of course, is the use of emulsifier mixtures.

The addition of the emulsifiers (b) to the formulation can be carried out in a known manner, directly, in aqueous solution or after thermal pretreatment of the mixture.

Depending on type (lipophilic or hydrophilic) and amount added, the emulsifiers can influence the functionality of the polymer layer.

Component (c)

Component (c): 5 to 50, preferably 10 to 20, % by weight (based on the component (a)) of a $C_{12}$- to $C_{18}$-monocarboxylic acid or of a $C_{12}$- to $C_{18}$-hydroxyl compound. The component (c) is crucial for the surprisingly low water vapour permeability of the formulations.

Unbranched $C_{12}$- to $C_{18}$-monocarboxylic acid or of a $C_{12}$- to $C_{18}$-hydroxyl compounds [sic] are preferred. Optionally, branched derivatives of the substances mentioned can also be suitable.

$C_{12}$- to $C_{18}$-monocarboxylic acids are, for example, in particular, lauric acid and myristic acid. Palmitic acid and stearic acid are preferred.

$C_{12}$- to $C_{18}$-hydroxyl compound, in particular alkanols having a terminal hydroxyl group such as, for example, lauryl alcohol or stearyl alcohol.

Further Additives

As a rule, during processing to give coating and binding agents customary additives are added to the formulation according to the invention.

The amounts employed and use of the customary additives in pharmaceutical films or coatings are familiar to the person skilled in the art. Customary additives can be, for example, release agents, pigments, stabilizers, antioxidants, pore formers, penetration promoters, lustre agents, aromatic substances or flavourings. They serve as processing aids and are intended to guarantee a safe and reproducible preparation process and good long-term storage stability or they achieve additional advantageous properties in the pharmaceutical form. They are added to the polymer preparations before processing and can influence the permeability of the coatings, which can optionally be utilized as an additional control parameter.

Release Agents:

Release agents as a rule have lipophilic properties and are added as a rule to the spray suspensions. They prevent agglomeration of the cores during film-coating. Preferably, talc, Mg or Ca stearate, ground silicic acid, kaolin or non-ionic emulsifiers having an HLB of between 3 and 8 are employed. Customary use amounts for release agents in the coating and binding agents according to the invention are between 0.5 to 100% by weight based on the copolymer (a).

In a particularly advantageous embodiment, the addition of the release agent takes place as a non-film-coating final layer. The application takes place as a powder (in concentrated form, 90–100% strength) or from aqueous suspension containing 5–30% solids content by spraying. The amount necessary is lower than in the case of incorporation into the polymer layer and is 0.1–2% based on the weight of the pharmaceutical form.

Pigments:

The addition only rarely takes place in the form of the soluble dye. As a rule, aluminium or iron oxide pigments are dispersed. Titanium dioxide serves as a white pigment. Customary use amounts for pigments in the coating and binding agents according to the invention [lacuna] between 20 and 60% by weight, based on the polymer mixture. Because of the high pigment binding power, however, amounts of up to 100% by weight can also be processed.

In a particularly advantageous embodiment, use of the pigment takes place as a non-film-coating final layer. The application takes place as a powder (in concentrated form, 90–100% strength) or from aqueous suspension containing 5–30% solids content by spraying. The amount necessary is lower than in the case of incorporation into the polymer layer and is 0.1–2% based on the weight of the pharmaceutical form.

In principle, of course, all substances employed must be toxicologically acceptable and be used in pharmaceuticals without risk for patients.

Further additives can also be plasticizers. Customary amounts are between 0 and 50, preferably 0 to 20, in particular 0 to 10, % by weight. Particularly preferably, however, at most 5% by weight of or no plasticizers are present, as the formulations are often already elastic enough due to the presence of the components (c) [sic] and additional plasticizers can lead to undesired stickiness.

Depending on type (lipophilic or hydrophilic) and amount added, plasticizers can influence the functionality of the polymer layer. Plasticizers achieve a lowering of the glass transition temperature by means of physical interaction with the polymer and, depending on the amount added, promote film-coating. Suitable substances as a rule have a molecular weight of between 100 and 20,000 and contain one or more hydrophilic groups in the molecule, e.g. hydroxyl, ester or amino groups.

Examples of suitable plasticizers are alkyl citrates, glycerol esters, alkyl phthalates, alkyl sebacates, sucrose esters, sorbitan esters, diethyl sebacate, dibutyl sebacate and polyethylene glycols 200 to 12,000. Preferred plasticizers are triethyl citrate (TEC), acetyltriethyl citrate (ATEC) and dibutyl sebacate (DBS). Mention may furthermore be made of esters which as a rule are liquid at room temperature, such as citrates, phthalates, sebacates or castor oil. Esters of citric acid and sebacic acid are preferably used.

The addition of the plasticizer to the formulation can be performed in a known manner, directly, in aqueous solution or after thermal pretreatment of the mixture. Mixtures of plasticizers can also be employed.

The Production Process

The components (a), (b) and (c) are blended with one another at ambient or elevated temperature with or without addition of water and if desired of a pharmaceutical active compound and the further customary additives and the coating and binding agent is prepared by melting, casting, spreading, spraying or granulating. The film-coating of the coating and binding agent here is a prerequisite for the functional effect in pharmaceutical forms.

The film-coating is carried out, independently of the application process, by supply of energy. This can take place via convection (heat), radiation (infrared or microwaves) or conduction. Water employed for application as a suspending agent evaporates here, and if desired a vacuum can also be used in order to accelerate the evaporation. The temperature necessary for the film-coating depends on the combination of the components employed.

Use of the Formulation According to the Invention for the Production of Binding Agents:

The use as binding agents is carried out, for example, by spraying the aqueous polymer suspension onto active-compound-free cores (nonpareilles) with simultaneous addition of powdered active compounds or mixtures thereof. A further embodiment is the spraying on of the aqueous polymer suspension together with active compounds dissolved or suspended therein.

Use of the Formulation According to the Invention for the Production of Coating Agents:

Preformed carriers for the coatings are capsules, tablets, granules, pellets, crystals of regular or irregular shape. The size of granules, pellets or crystals is between 0.01 and 2.5 mm, that of tablets between 2.5 and 30.0 mm. Capsules consist of gelatine, starch or cellulose derivatives.

As a rule, powders and crystals contain 100% of the biologically active substance. Preformed carriers contain from about 0.1 to 99% of the biologically active substance or of the pharmaceutical active compound and to [sic] 1 to 99.9% by weight of further pharmaceutical excipients.

Customary preparation processes are direct compression, compression of dry, moist or sintered granules, extrusion and subsequent rounding, moist or dry granulation or direct pelletting (e.g. on plates) or by binding of powders (powder layering) to active-compound-free spheres (nonpareilles) or active-compound-containing particles.

In addition to the active compound, they can contain further pharmaceutical excipients: binding agents, such as cellulose and its derivatives, polyvinylpyrrolidone (PVP), moisturizing agents, disintegration promoters, lubricants, disintegrants, (meth)acrylates, starch and its derivatives, sugar solubilizers or others.

Of particular importance is the disintegration time of the cores, which influences the release of the active compound. Today, short disintegration times of below 5, or below 10 min, are demanded in the disintegration test according to Ph. Eur. Longer disintegration times are therefore problematical, because additional coatings further delay the release of the active compound and can call the therapeutic effect into question. The threshold value today is regarded as a disintegration time of 30 min. Testing is carried out in water and artificial gastric juice (0.1 N HCl). The cores employed are homogeneous or have a layered structure. If engravings are embedded in the surfaces, as far as these should be covered possible by coatings but only slightly filled in. The layer thickness employed according to the invention of the polymer powder varies greatly and depends on the processing procedure or the amount of additives. It is between 1 and 100 μm, preferably between 10 and 50 μm. On customary tablets, this corresponds to a polymer application of 0.5 to 5% by weight.

Coated microparticles can be compressed according to K. Lehmann et al., Drugs made in Germany 37, 2, 53–60 (1994) and T. E. Beckert et al., International Journal of Pharmaceutics 143, (1996), 13–23 to give disintegrating tablets without significant influence on the function of the polymer.

The function of the film-coated polymer layer in the final pharmaceutical form can be varied:
 Protection against harmful environmental influences due to moisture, gases, light etc.
 Odour or taste isolation
 Marking by means of colour
 Mechanical stabilization
 Isolation of incompatible ingredients
 Avoidance of adhesion to the mucous membranes
 Temporally delayed release of active compound
 pH-controlled release of active compound
 Isolation of cores from further coatings The low viscosity of the polymer mixture in aqueous dispersion is advantageous even at high solid contents of up to 30%, as engravings on the surface of tablets are reproduced in detail.

Particularly advantageous is the good protective and isolating action of the polymer mixture according to the invention with simultaneously low influence on the tablet disintegration. Even with low polymer applications of 1% by weight, a taste isolation of more than 30 sec is already achieved. Thicker coatings with a copolymer of methyl methacrylate, butyl methacrylate and dimethylaminoethyl methacrylate in the ratio 25:25:50 (EUDRAGIT®EPO) improve the taste concealment, but without prolonging the disintegration time in 0.1 N HCl. Likewise advantageous is the permissible covering of coloured cores by coatings with a high pigment content. One particular embodiment is the embedding of a second active compound in the coating on an active-compound-containing core.

Application to the Formulation According to the Invention for Production on Carriers The formulation according to the invention can be applied by granulating, pouring, spreading or by means of spray application in powder form, as a melt or in aqueous suspension. Water is here used mainly as a vehicle in order to apply thin coatings uniformly on spherical cores, e.g. by spraying. For coatings, spreading processes are moreover employed. The process employed depends mainly on the carrier chosen. Dry powders are applied by spreading or dusting, if appropriate also using electrostatic forces. The film-coating can take place by the action of heat. For implementation it is crucial here that uniform, closed layers are formed.

For application processes according to the prior art see, for example, Bauer, Lehmann, Osterwald, Rothgang, "Überzogene Arzneiformen" (Coated Pharmaceutical Forms") Wissenschaftliche Verlagsgesellschaft mbH Stuttgart, Chap. 7, pp. 165–196.

Properties relevant to application, tests required and specifications are listed in pharmacopoeias.

Details can be taken from the customary textbooks, e.g.:

Voigt, R. (1984): Lehrbuch der pharmazeutischen Technologie (Textbook of Pharmaceutical Technology); Verlag Chemie Weinheim—Beerfield Beach/Florida—Basle.

Sucker, H., Fuchs, P., Speiser, P.: Pharma-zeutische Technologie (Pharmaceutical Technology), Georg Thieme Verlag Stuttgart (1991), in particular Chapter 15 and 16, pp. 626–642.

Gennaro, A. R. (Editor), Remington's Pharmaceutical Sciences, Mack Publishing Co., Easton, Pa. (1985), Chapter 88, pp. 1567–1573.

List, P. H. (1982): Arzneiformenlehre (Pharmaceutical Form Theory), Wissenschaftliche Verlagsgesellschaft mbH, Stuttgart.

Biologically Active Substances:

The pharmaceutical substances employed for the purpose of the invention are intended to be used on or in the human or animal body in order 1. to cure, to alleviate, to prevent or to detect diseases, suffering, bodily injury or pathological symptoms.
2. to be able to recognize the condition, the state or the function of the body or mental states.
3. to replace active compounds or bodily fluids produced by the human or animal body.
4. to defend against, to eliminate or to render harmless pathogens, parasites or exogenous substances or
5. to influence the condition, the state or the function of the body or mental states.

Customary pharmaceuticals can be taken from reference works, such as the Rote Liste or the Merck Index. The formulation according to the invention is suitable for the administration of fundamentally any desired pharmaceutical active compounds which can preferably be administered in isolated or protected form, such as antidepressants, beta-receptor blockers, antidiabetics, analgesics, antiinflammatories, antirheumatics, antihypotensives, antihypertensives, psychopharmaceuticals, tranquillizers, antiemetics, muscle relaxants, glucocorticoids, agents for the treatment of ulcerative colitis or Crohn's disease, antiallergics, antibiotics, antiepileptics, anticoagulants, antimycotics, antitussives, arteriosclerotic agents, diuretics, enzymes, enzyme inhibitors, antigout agents, hormones and their inhibitors, cardiac glycosides, immunotherapeutics and cytokines, laxatives, hypolipidaemics, gastrointestinal therapeutics, antimigraine agents, mineral preparations, otologicals, antiparkinson agents, thyroid gland therapeutics, spasmolytics, platelet aggregation inhibitors, vitamins, cytostatics and metastasis inhibitors, phytopharmaceuticals, chemotherapeutics and amino acids. Examples of suitable active compounds are acarbose, nonsteroidal antirheumatics, cardiac glycosides, acetylsalicylic acid, virustatics, aclarubicin [sic], acyclovir, cisplatin, actinomycin, alpha- and beta-sympathomimetics, (allopurinol [sic], alosetrone, alprostadil, prostaglandins, amantadine, ambroxole, amlodipine, methotrexate, S-aminosalicylic acid, amitriptyline, amlodipine [sic], amoxicillin, anastrozole, atenolol, atorvastatin, azathioprine, balsalazide, beclo-methasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins [sic], celetoxib, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimazole, codeine, caffeine, vitamin D and derivatives of vitamin D, colestyramine, cromoglycic acid, coumarin and coumarin derivatives, cysteine, cytarabine, cyclophosphamide, cyclosporin, cyproterone, cytarabine [sic], dapiprazole, desogestrel, desonide, dihydralazine, diltiazem, ergot alkaloids, dimenhydrinate, dimethyl sulphoxide, dimeticone [sic], dipyridarnoi [sic], domperidone and domperidan [sic] derivatives, donepzil, dopamine, doxazosine, doxorubicin, doxylamine, dapiprazole [sic], benzodiazepines, diclofenac, glycoside antibiotics, desipramine, econazole, ACE inhibitors, enalapril, ephedrine, epinephrine. epoetin and epoetin derivatives, morphinans, calcium antagonists, irinotecan, modafinil, orlistate, peptide antibiotics, phenytoin, riluzole, risedronate, sildenafil, topiramate, macrolide antibiotics, esomeprazole, oestrogen and oestrogen derivatives, gestagen and gestagen derivatives, testosterone and testosterone derivatives, androgen and androgen derivatives, ethenzamide, etofenamate, etofibrate, fenofibrate, etophylline, etoposide, famciclovir, famotidine, felodipine, fenofibrate, fentanyl, fenticonazole, gyrase inhibitors, fluconazole, fludarabine, flunarizine, fluorouracil, fluoxetin, flubiprofen, ibuprofen, flutamide, fluvastatin, follitropin, formoterol, fosfomycin, furosemide, fusidic acid, galantamine, gallopamil, ganciclovir, gemfibrozil, gentamicin, ginkgo, St. John's wort, glibenclamide, urea derivatives as oral antidiabetics, glucagon, glucosamine and glucosamine derivatives, glutathione, glycerol and glycerol derivatives, hypothalamic hormones, goserelin, gyrase inhibitors [sic], guanethidine, halofantrin, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indomethacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotilin, mebendazole, mebeverine, meclozine, mefenamic acid, mefloquin, meloxicam, mepindolol, meprobamate, meropenem, mesalazine, mesuximide, metamizole, metformin, methotrexate, methylphenidate, methylprednisolone, metixen, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulphone, noscapine, nystatin, ofloxacin, olanzapine, olsalazine, omeprazole, omoconazole, odansetrone, orlistat, oseltamivir, oxaceprol, oxacillin, oxiconazole, oxymetazoline, pantoprazole, paracetamol, paroxetin, penciclovir, oral penicillins, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexol, pravastatin, prazosine, procaine, promazine, propiverine, propranolol, propyphenazone, prostaglandins, protionamide, proxyphylline, quetiapine, quinapril, quinaprilate, ramipril, ranitidine, reproterol, reserpine, ribavirin, rifampicin, risperidone, ritonavir, ropinirol, rosiglitazone, roxatidine, roxithromycin, ruscogenin, rutoside and rutoside derivatives, sabadilla, salbutamol, salmeterol, scopolamine, selegenin, sertaconazole, sertindole, sertralione [sic], silicates, simvastatin, sitosterin, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrin, tacrolimus, taliolol, tamoxifen, taurolidine, tazorotene, tegaserod, temazepam, teniposide, tenoxicam, terazosine, terbinafine, terbutaline, terfenadine, terlipressin, tertatolol, tetracyclines, tetryzoline, theobromine, theophylline, butizine, thiamizole, phenothiazines, thiotepa, tiagabine, tiapride, propionic acid derivatives, ticlopidine, timolol, tinidazole, tioconazole, tioguanine, tioxolone, tiropramide [sic], tizanidine, tolazoline, tolbutamide, tolcapone, tolnaftate, tolperisone, topotecan, torasemide, anti6strogens [sic], tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpine, troxerutine, tulobuterol, tyramine, tyrothricin, urapidil, ursodeoxycholic acid [sic], chenodeoxycholic acid [sic], valaciclovir, valdecoxib, valproic acid, vancomycin, vecuronium chloride, venlafaxin, verapamil, vidarabin, vigabatrin, viloxazine, vinblastine, vincamine, vincristine, vindesine, vinorelbin, vinpocetin, viquidil, warfarin, xantinol nicotinate, xipamide, zafirlukast, zalcitabin, zanamivir, zidovudine, zolmitriptan, zolpidem, zoplicone, zotepine and the like.

If desired, the active compounds can also be used in the form of their pharmaceutically acceptable salts or derivatives, and in the case of chiral active compounds both optically active isomers and racemates or diastereoisomer mixtures can be employed. If desired, the compositions according to the invention can also contain two or more pharmaceutical active compounds.

Examples of particularly preferred active compounds acetylsalicylic acid, cabenoxolone, cefalotin, epinefrine [sic], imipramine, potassium iodide, ketoprofen, levodopa, nitrazepam, nitroprusside, oxytetracycline HCl, promethazine, omeprazole or other benzimidazole derivatives and streptomycin.

Administration Forms:

In principle, the pharmaceutical forms described can be used directly by oral administration. The granules, pellets or particles prepared according to the invention can be dispensed in gelatine capsules, sachets or in suitable multi-dose containers having a dosage device. Administration is carried out in solid form or suspended in liquids. By means of compression, if applicable after admixture of further excipients, tablets are obtained from which disintegrate after administration and which release usually coated subunits. Likewise conceivable is the embedding of agglomerates in polyethylene glycol or lipids for the production of suppositories or vaginal pharmaceuticals. Coated tablets are packed in blister packs or multi-dose containers and removed by the patient directly before administration.

Active compound classes and substances which can often produced a bitter taste and can be formulated advantageously using the coating and binding agents according to the invention are, for example:

Analgesics and antirheumatics:
  paracetamol, diclofenac, aceclofenac, ibuprofen, ketoprofen, flurbiprofen, levacetylmethadol, oxycodone
Psychopharmaceuticals:
  prometazine, donepizil, modafinil, nefazodone, reboxetin, sertindole, sertralin
Antibiotics:
  erythromycin, roxithromycin, clarithromycin, grepafloxacin, ciprofloxacin, levofloxacin, sparfloxacin, trovafloxacin, nevirapin
Beta-blockers
  propranolol, metoprolol, bisoprolol, nebivolol
Antidiabetics:
  metformin, miglitol, repaglinide
H1 antihistaminics
  diphenhydramine, fexofenadine, mizolastine
H2 antihistaminics
  cimetidine, nizatidine, ticlopidine, cetridine, ranitidine
Vitamins: thiamine nitrate; Others: quinidine sulphate, amiloprilose HCl, pseudoephedrine HCl, sildenafil, topiramate, granisetrone, rebamipide, quinine HCl

EXAMPLES

Examples 1 to 14

Dispersion or dissolution of a copolymer of methyl methacrylate, butyl methacrylate and dimethylaminoethyl methacrylate in the ratio 25:25:50 with an average particle size of 15 μm (EUDRAGIT® E PO).

Preparation Procedure:

Completely demineralized water is preadded to a vessel then the components (a), (b) and (c) according to claim 1 added with stirring by means of a bladed stirrer stirred at about 400 revolutions/min [sic]. The entire preparation is monitored [lacuna] 400 times magnification using a polarization microscope.

The dispersion or solution has a dry matter content of 15%, and is of low viscosity.

Example 15: a copolymer of methyl methacrylate, butyl methacrylate, and dimethylamino ethyl methacrylate in the ratio 25:25:50 (EUDRAGIT® E100) dissolved in isopropanol/acetone (6:4) is used. Copolymer content 12.5% by weight.

The experiments listed below in Table 1 are calculated on a batch size of 100 g, the additions being relative to the amount of copolymer.

Abbreviations:
rel. to=relative to
RT=room temperature

TABLE 1

Preparation of the coating and binding agent

| Example No. | Component (b) [% rel. to copolymer] | Component (c) [% rel. to copolymer] | Dispersing temperature | Dispersing time [h] | Dispersion complete | Properties of the dried films | WVP [g/m²/d] |
|---|---|---|---|---|---|---|---|
| 1. | 7 Na lauryl sulphate | 15 lauric acid | RT | about 3 | yes | flexible, clear | 324 |
| 2. | 7 Na lauryl sulphate | 15 myristic acid | RT | about 4 | yes | flexible, slightly clouded | 324 |
| 3. | 7 Na lauryl sulphate | 15 palmitic acid | RT | about 6 | yes | flexible, slightly clouded | 168 |
| 4. | 7 Na lauryl sulphate | 15 stearic acid | RT | about 6 | yes | flexible, slightly clouded | 179 |
| 5. | 7 Na lauryl sulphate | 20 stearic acid | RT | about 6 | yes | flexible, slightly clouded | 213 |
| 6. | 7 Na lauryl sulphate | 30 stearic acid | RT | about 5 | yes | flexible, slightly clouded | 289 |
| 7. | 7 Na lauryl sulphate | 30 stearic acid | RT to 73° C. | about 4 | yes | flexible, slightly clouded | 186 |
| 8. | 10 Na lauryl sulphate | 10 stearic acid | RT | about 6 | yes | flexible, slightly clouded | 125 |
| 9. | 10 Na lauryl sulphate | 15 stearic acid | RT | about 6 | yes | brittle, slightly clouded | 96 |
| 10. | 10 Na lauryl sulphate | 15 lauryl alcohol | RT | about 24 | yes | flexible, clear | 264 |
| 11. | 10 Na lauryl sulphate | 10 lauryl alcohol | RT | about 3 | yes | flexible, clear | 112 |

Negative Examples

| Example No. | Component (b) [% rel. to copolymer] | Component (c) [% rel. to copolymer] | Dispersing temperature | Dispersing time [h] | Dispersion complete | Properties of the dried films | WVP [g/m²/d] |
|---|---|---|---|---|---|---|---|
| 12. | 7 Na lauryl sulphate | 15 sebacinic acid | RT | about 2 | yes | brittle crystals | 454 |
| 13. | 7 Na lauryl sulphate | 15 behenic acid | RT | — | no | — | — |
| Prior art | | | | | | | |
| 14. | 7 Na lauryl sulphate | 15 diethyl sebacate | | | | | 444 |
| 15. | — | — | EUDRAGIT ® E 12.5 from organic solution (isopropanol-acetone = 6:4) | | | | 336 |

Water Vapour Permeabilities, Film Properties

Films of the dispersions prepared are drawn on condenser paper by means of a 250 μm doctor blade and allowed to dry overnight at RT. The dried films having a layer thickness of 30–35 μm (condenser paper additionally included) are then investigated for water vapour permeability according to DIN 53122 at 23° C., 85% relative humidity. For each dispersion, 6 tests are carried out in parallel.

Description of the Test:

3 g of silica gel, granulation 1–3 mm/Merck, having a moisture indicator, are weighed into a plane-ground test cell made of glass (internal diameter 2 cm) and dried at 110° C. for 3 hours. The ground surface of the test cell is greased with silicone paste so that after application of the film an airtight closure is guaranteed. The selected films [lacuna] applied and covered with a likewise plane-ground silicone-greased glass ring. By means of this film surface of 3.14 cm² which is now formed, the water vapour permeability (WVP) at 23° C. and 85% rel. humidity is determined gravimetrically over a period of time of 16 and 24 hours.

$$WVD(g/m^2/d) = 24/t \times \Delta m/A \times 24$$

t=experimental time in hours between the weighings from which the weight difference Δm is determined, i.e. 18−2=16 or 24−2=22

Δm=amount of water diffused through the film in g after 16 hours and 22 hours; the weight of the test cell+film obtained after 2 hours counts as a reference value.

A=test area of the film in cm²=3.14 cm²

The average value is calculated from the results (16 and 22 h) of at least 5 test cells.

Coatings from the Dispersions of the above Examples

The spray experiments were carried out in an Erweka coating pan with 2.5 to 3 kg batch size placebo tablets, partly replaced by quinidine sulphate tablets or silica gel tablets. The polymer application is 2 to 4 mg/cm².

The release agent is manly homogenized in the dispersion by means of an Ultra Turrax for about 15 min and then sprayed onto the rotating tablets using a two-channel spray pistol Walter NBA nozzle 1.2 mm, spray pressure of 0.8 to 1 bar. The material temperature can be between 27 to [sic] 34° C., while the spray velocity can be 2.2 to 3 g/min/kg. Drying is then carried out in a 40° C. recirculating drying oven for 4 h.

TABLE 2

| Run No. | Experiment according to recipe no. | Release agent (% rel. to Copo) | mg of Copo/cm² | Disintegration time (min) MS | H₂O | Taste isolation |
|---|---|---|---|---|---|---|
| 16. | 4. | 42 pigment | 2 | 2.1 | 5.3 | >8 min |
| 17. | 4. | 50 talc | 2 | 1.3 | 3.6 | n. d. |
|  |  |  | 4 | 1.7 | 7.3 | n. d. |
| 18. | 14. | 35 Mg stearate | 2 | 1.7 | 17.2 | n. d. |
|  |  |  | 4 | 2 | 21.5 | n. d. |
| 19. | 8. | 15 Mg stearate 15 pigments | 2 | 1.2 | 2.2 | >6 min |
| 20. | 15. | 50 talc | 2 | 1.1 | >60 | n. d. |
|  |  |  | 4 | 1.7 | >60 | n. d. |
| 21. | 4. | 35 Mg stearate | 2 | 1.7 | 3.9 | n. d. |
|  |  |  | 4 | 1.97 | 6.4 | n. d. |

Copo = copolymer

The disintegration time was determined following according to [sic] the method of the European pharmacopoeia.

TABLE 3

Water absorption of silica gel tablets in an air-conditioned cabinet at 40° C. and 75% rel. humidity with 4 mg of copolymer/cm².

| Recipe | Water absorption [%] | | | | | |
|---|---|---|---|---|---|---|
|  | after 1 h | after 2 h | after 4 h | after 6 h | after 10 h | after 24 h |
| According to Example 20 | 0.48 | 1.07 | 2.16 | 3.04 | 4.80 | 9.06 |
| According to Example 18 | 0.67 | 1.62 | 2.71 | 3.79 | 5.93 | 11.19 |
| According to Example 21 | 0.34 | 0.69 | 1.36 | 1.92 | 3.11 | 6.55 |
| Comparison value: HPMC | 2.68 | 5.31 | 9.46 | 12.30 | 14.80 | 15.10 |
| Comparison value: silica gel tablets (without coating) | 7.71 | 11.94 | 14.61 | 15.10 | 15.16 | 15.64 |

The water absorption was determined gravimetrically.

The invention claimed is:

1. A process for producing a coating and binding agent comprising:
   (a) 50 to 90% by weight, of a copolymer comprising free-radical-polymerized C1 to C4 esters of acrylic or methacrylic acid and (meth)acrylate monomers which contain functional tertiary amino groups, wherein the copolymer is present in powder form having an average particle size of 1–40 μm,
   (b) 3 to 15% by weight, based on (a), of an emulsifier having an HLB of at least 14, and
   (c) 5 to 50% by weight, based on (a), of a $C_{12}$- to $C_{18}$-monocarboxylic acid or a $CH_3(CH_2)_nOH$ compound where n is from 11 to 17, said process comprising, blending or mixing (a), (b) and (c) with or without addition of water, a pharmaceutical active compound, one or more additives or mixtures thereof, and forming the coating and binding agent by melting, casting, spreading, spraying or granulating, wherein the coating and binding agent has a water vapor permeability of at most 300 (g/m$^2$/d) as measured according to DIN 53 122.

2. The process according to claim 1, further comprising applying a release agent to the coating and binding agent.

3. The process according to claim 1, further comprising applying a pigment to the coating and binding agent.

4. A coating and binding agent prepared by the process according to claim 1.

5. A pharmaceutical form comprising the coating and binding agent according to claim 4 and a pharmaceutical active compound.

6. The pharmaceutical form according to claim 5, comprising a moisture-sensitive pharmaceutical active compound selected from the group consisting of analgesics, antirheumatics, active compounds for the treatment of gastric ulcers, antibiotics, antihypotensives, antidepressants, thyroid gland therapeutics, antiparkinson active compounds, anxiolytics and neuroleptics.

7. The pharmaceutical form according to claim 6, wherein the moisture-sensitive pharmaceutical active compound is selected from the group consisting of acetylsalicylic acid, carbenoxolone, cefalotin, epinefrine, imipramine, potassium iodide, ketoprofen, levodopa, nitrazepam, nitroprusside, oxytetracycline HCl, promethazine, omeprazole, benzimidazole derivatives and streptomycin.

8. A method comprising coating a pharmaceutical composition with the coating and binding agent of claim 4.

9. A moisture-isolating coating comprising the coating and binding agent according to claim 4.

10. A taste-isolating coating comprising the coating and binding agent of claim 4.

11. The coating and binding agent of claim 4, comprising a $C_{12}$- to $C_{18}$-monocarboxylic acid;
wherein the $C_{12}$- to $C_{18}$-monocarboxylic acid is lauric acid.

12. The coating and binding agent of claim 4, comprising a $C_{12}$- to $C_{18}$-monocarboxylic acid;
wherein the $C_{12}$- to $C_{18}$-monocarboxylic acid is myristic acid.

13. The coating and binding agent of claim 4, comprising a $C_{12}$- to $C_{18}$-monocarboxylic acid;
wherein the $C_{12}$- to $C_{18}$-monocarboxylic acid is palmitic acid.

14. The coating and binding agent of claim 4, comprising a $C_{12}$- to $C_{18}$-monocarboxylic acid;
wherein the $C_{12}$- to $C_{18}$-monocarboxylic acid is stearic acid.

15. The coating and binding agent of claim 4, comprising a $CH_3(CH_2)_n OH$ compound;
wherein the $CH_3(CH_2)_n OH$ compound is lauryl alcohol.

16. The coating and binding agent of claim 4, comprising a $CH_3(CH_2)_n OH$ compound;
wherein the $CH_3(CH_2)_n OH$ compound is stearyl alcohol.

17. The process of claim 1, wherein the coating and binding agent has a water vapor permeability of at most 200 (g/m$^2$/d) as measured according to DIN 53 122.

18. The coating and binding agent of claim 4, which has a water vapor permeability of at most 200 (g/m$^2$/d) as measured according to DIN 53 122.

19. The process of claim 1, wherein (a), (b), (c) are blended with the addition of the pharmaceutical active compound.

20. The process of claim 1, wherein (a), (b), (c) are blended without the addition of the pharmaceutical active compound.

* * * * *

UNITED STATES PATENT AND TRADEMARK OFFICE
CERTIFICATE OF CORRECTION

PATENT NO. : 7,160,558 B2
APPLICATION NO. : 10/239634
DATED : January 9, 2007
INVENTOR(S) : Hans-Ulrich Petereit et al.

Page 1 of 1

It is certified that error appears in the above-identified patent and that said Letters Patent is hereby corrected as shown below:

On The Title Page, Item -57-
ABSTRACT, line 7, "coplymer being present"
    should read -- copolymer being present --;
  line 10, "of a $C_{12}$—to"
    should read -- of a $C_{12}$- to --;
  line 11, "carboxylic acid or a $C_{12}$—to"
    should read -- carboxylic acid or $C_{12}$- to --.

Column 3, line 22, "measurement in liquids is the the"
    should read -- measurement in liquids is that the --;
  line 45, "Pat. No. 4,795,643 (Seth))."
    should read -- Pat. No. 4,795,643 (Seth). --.

Column 8, line 42, "epinephrine. epoetin and"
    should read -- epinephrine, epoetin and --.

Column 12, line 52, "[g/m[hu 2/d]" should read -- $[f/m^2/d]$ --;
  line 54, "brittle" should read -- Brittle --.

Column 13, line 64, "release agent is manly homogenized"
    should read -- release agent is mainly homogenized --.

Signed and Sealed this

Twelfth Day of June, 2007

JON W. DUDAS
*Director of the United States Patent and Trademark Office*